(12) United States Patent
Rutkowski

(10) Patent No.: US 8,388,579 B2
(45) Date of Patent: Mar. 5, 2013

(54) DEVICE FOR VEIN STABILIZATION

(76) Inventor: James Louis Rutkowski, Clarion, PA (US)

( * ) Notice: Subject to any disclaimer, the term of this patent is extended or adjusted under 35 U.S.C. 154(b) by 0 days.

(21) Appl. No.: 13/204,439

(22) Filed: Aug. 5, 2011

(65) Prior Publication Data

US 2012/0035554 A1 Feb. 9, 2012

Related U.S. Application Data

(63) Continuation of application No. 11/853,221, filed on Sep. 11, 2007, now Pat. No. 8,007,467.

(60) Provisional application No. 60/844,007, filed on Sep. 12, 2006.

(51) Int. Cl.
*A61M 5/00* (2006.01)
(52) U.S. Cl. ........................................ 604/115; 604/116
(58) Field of Classification Search .................. 604/115, 604/116, 180; 606/108, 158
See application file for complete search history.

(56) References Cited

U.S. PATENT DOCUMENTS

| | | | | | |
|---|---|---|---|---|---|
| 1,561,115 | A | * | 11/1925 | Ruddick | 340/309 |
| 2,704,071 | A | * | 3/1955 | Becker | 604/115 |
| 4,223,673 | A | * | 9/1980 | Harris | 604/115 |
| 5,175,933 | A | * | 1/1993 | Shepherd | 30/322 |
| 6,156,008 | A | * | 12/2000 | Castellano | 604/116 |
| 6,673,091 | B1 | * | 1/2004 | Shaffer et al. | 606/201 |
| 2004/0015130 | A1 | * | 1/2004 | Neumann et al. | 604/116 |

* cited by examiner

*Primary Examiner* — Nicholas Lucchesi
*Assistant Examiner* — Gerald Landry, II
(74) *Attorney, Agent, or Firm* — Reed Smith LLP

(57) ABSTRACT

Apparatuses and methods for performing and aiding venipuncture. The apparatuses of the present invention provide the medical practitioner with an improved tool for performing venipuncture methods. The apparatus preferably includes a handle that is connected to a plurality of tines that run roughly parallel to one another. During use, the tines of the apparatus are pressed against the skin of the patient such that they sit astride the vein to be accessed. The distance between the various tines of the present apparatuses varies so as to be able to accommodate a variety of vein widths. The apparatuses of the present invention may have tines at either one or both ends of the body of the apparatus. The apparatuses of the present invention may be used with a variety of vein accentuating devices, such as those that employ light to accentuate the vein to be punctured.

14 Claims, 5 Drawing Sheets

DEVICE FOR VEIN STABILIZATION

CROSS-REFERENCE TO RELATED APPLICATION

This Application is a continuation of U.S. application Ser. No. 11/853,221, filed Sep. 11, 2007, now U.S. Pat. No. 8,007,467 application claims the benefit under 35 U.S.C. §119(e) of the earlier filing date of U.S. Provisional Application Ser. No. 60/844,007, now abandoned, filed on Sep. 12, 2006 which is hereby incorporated by reference.

BACKGROUND OF THE INVENTION

1. Field of the Invention

The field of the present invention generally relates to devices that aid a practitioner in performing efficient and safe venipuncture for starting intravenous solutions and/or blood draws.

2. Description of the Background

A common medical procedure is the insertion of a surgical cannula or syringe needle into a blood vessel or artery of a patient to obtain a blood sample, deliver a drug, or to perform diagnostic tests. In the insertion of a needle into a vein, the needle is positioned directly over the selected vein at an angle that is selected to avoid pushing the needle completely through the vein, while at the same time positioning the needle so that fluids may be delivered to or blood removed from the patient.

In performing a venipuncture, the medical professional always seeks to accomplish the task of inserting the needle on the first trial. However, the medical practitioner is routinely confronted with difficulties in obtaining venous access to patients. In some circumstances, the practitioner will miss the vein with the needle, resulting in an unsightly mark and a painful injury for the patient. One of the common causes of poor venous access is vein instability where veins roll away from the needle. In other circumstances, the practitioner may also have a difficult time in seeing the vein.

While tools in the prior art have attempted to address this problem, the solutions have all proved unsatisfactory for a variety of reasons. Some pieces of prior art (e.g., U.S. Pat. No. 3,324,854) that are designed to facilitate the insertion of a hypodermic syringe needle employ an apparatus that is attached to the body of the syringe. Such tools are limited in their applicability by the mechanism by which they attach to the syringe body. Other prior art devices (e.g., U.S. Pat. No. 5,415,647) are designed to allow the medical practitioner to immobilize veins by pinching the skin surface around the vein. Such procedures take time to execute and slow down the medical practitioner. Furthermore, the device itself may occlude the vein from the medical professional's sight, thereby potentially making venipuncture more difficult.

Thus, there has been a long standing need in the medical field for a vein stabilizer that is adaptable to various vein and skin types while at the same time not requiring specialized techniques to be employed. Such a vein stabilizer would also preferably accentuate the vein so that the medical practitioner would be able to obtain venous access reliably and efficiently. The present invention addresses these needs.

SUMMARY OF THE INVENTION

The present invention encompasses apparatuses and methods for performing and aiding venipuncture. The apparatuses of the present invention preferably include a handle that is connected to a plurality of tines that run roughly parallel to one another. During use, the tines of the apparatus are pressed against the skin of the patient such that they sit astride the vein to be accessed. The distance between the various tines of the present apparatuses varies so as to be able to accommodate a variety of vein widths. In certain preferred embodiments, sets of tines are located on both ends of the apparatus to provide the medical practitioner with many intra-tine distances from which to select. The apparatuses of the present invention may be used with a variety of vein accentuating devices, such as those that employ light to accentuate the vein to be punctured. The present invention thus acts as a needle director. By having roughly parallel tongs on each side of the vein, the present invention helps the practitioner to direct the needle, catheter, or butterfly into the vein, and further prevents the vein from rolling during venipuncture.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided hereinbelow with reference to the attached drawings.

The present invention is beneficial in aiding a medical professional in performing venipuncture for starting intravenous solutions, blood draws, or in performing diagnostic tests. The present invention preferably acts as a vein accentuator, a vein locator, a vein stabilizer, and a needle director.

Figure 1:
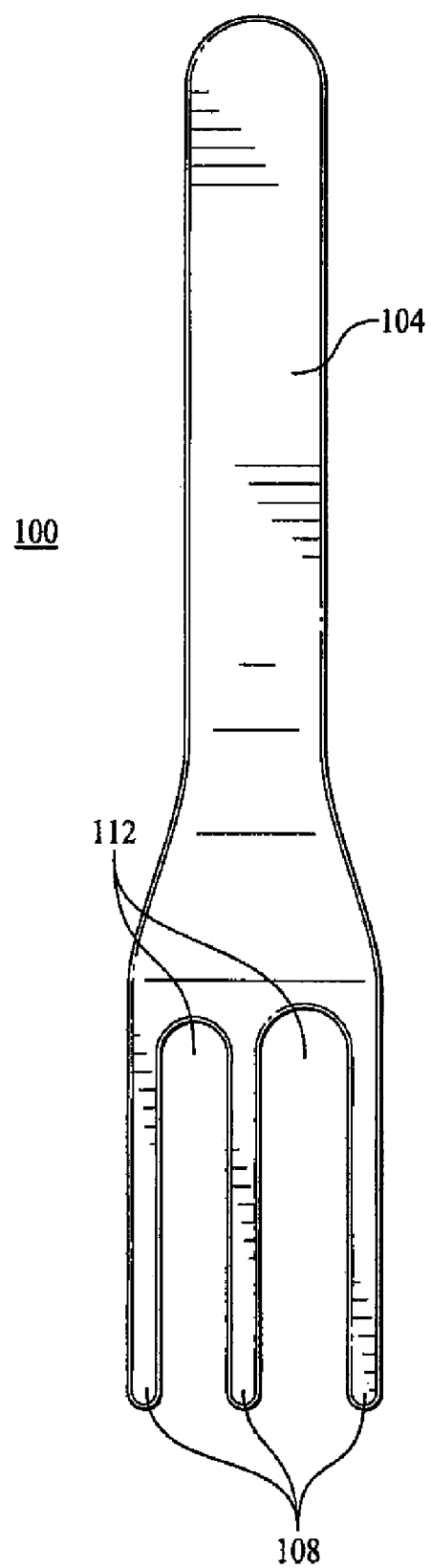
FIG. 1 depicts a top view of a first embodiment of the present invention.

A presently preferred embodiment of the present invention is shown in FIG. 1. In this embodiment 100, the device of the present invention resembles a "pitch fork." The apparatus 100 preferably includes a handle 104 that is connected to a plurality of tines 108 that run roughly parallel to one another. The spacing between the tines 112 varies so as to accommodate veins of more than one diameter as described hereinbelow. The distance between the tines ranges from about 6 millimeters to about 9 millimeters. While the embodiment in FIGS. 1-3 possesses three tines, the present invention also encompasses embodiments with different number of times (e.g., 4 or more tines). In presently preferred embodiments, the tines range from about 2.5 centimeters to about 5 centimeters with 4 centimeters being preferred.

Figure 2:
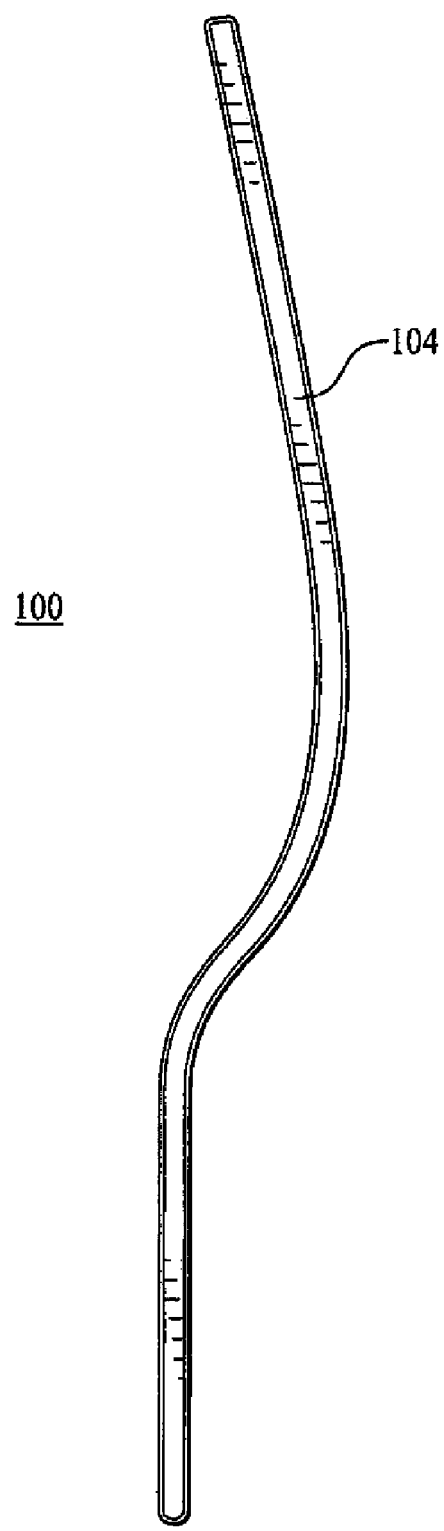
FIG. 2 shows a side view of a first embodiment of the present invention.

FIG. 2 displays a side view of the embodiment 100 shown in FIG. 1. As shown, the handle 104 preferably has a slight curve to it. As described more fully below, the curvature allows a medical practitioner to apply a slight pressure to the patient's skin during operation.

Figure 3:
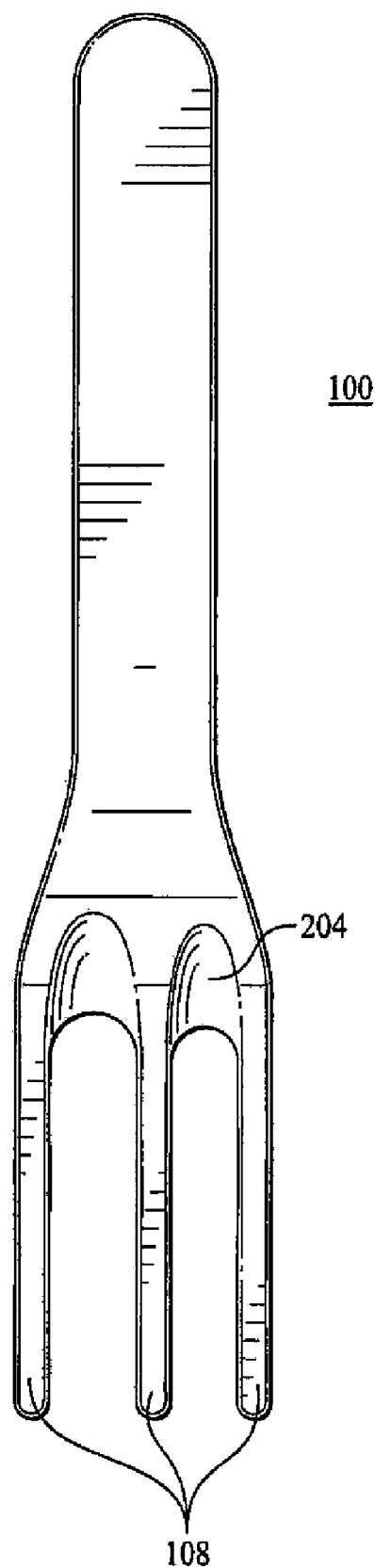
FIG. 3 displays the reverse side of a first embodiment of the present invention.

FIG. 3 shows a bottom view of the embodiment 100 shown in FIG. 1. As indicated, a portion 204 of the reverse side of the apparatus 100 that is located between the tines 108 may be hollowed out so as to accommodate the vein that is being accessed. This property may optionally be included and embodiments lacking this feature are further contemplated as within the scope of the present invention.

During use of the present invention, the device 100 is pressed against the skin of the patient with the tines 108 of the device on either side of the vein to be accessed. The slight curve of the handle 104 enables the practitioner to apply pressure to the tines 108 of the apparatus 100 that is transferred to each side of a vein. The applied pressure result in an accentuation of the vein further providing the practitioner with a clear target for venipuncture.

The present invention further acts as a needle director. By having roughly parallel tongs on each side of the vein, the present invention helps the practitioner to direct the needle, catheter, or butterfly into the vein. The practitioner simply directs the needle down the center of the tines that are on each side of the vein. The present invention does not require any special techniques to be performed, but may rather be used during the standard course of procedures.

Figure 4:
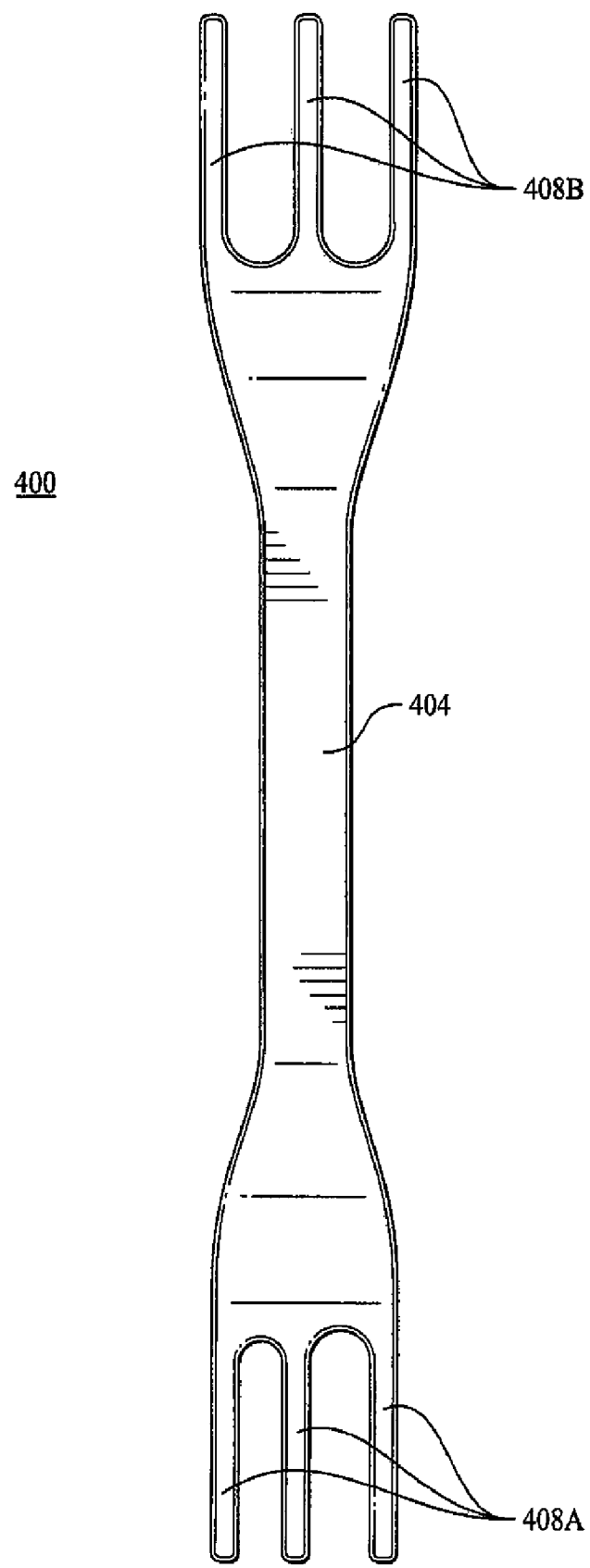
FIG. 4 depicts a top view of a second embodiment of the present invention.
Figure 5:
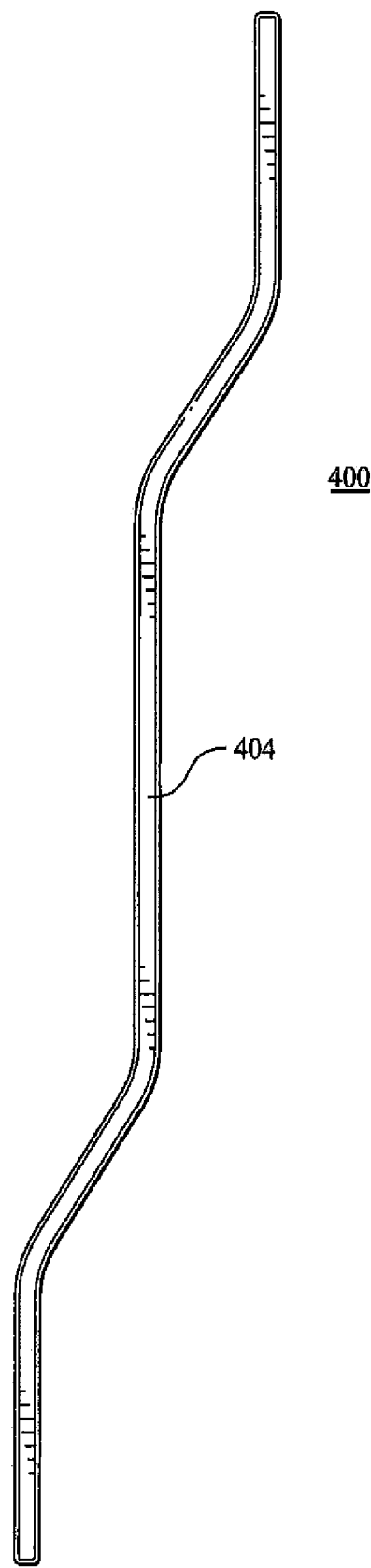
FIG. 5 shows a side view of a second embodiment of the present invention.

FIG. 4 shows a second preferred embodiment 400 of the present invention. In this embodiment, the apparatus 400 has a single handle 404 with two sets of tines 408A and 408B that are preferably located on opposite sides of the apparatus 400. Preferably, the spacing between tines 408B and 408A varies so that the apparatus 400 can accommodate a diversity of vein dimensions while being contained in a single apparatus. FIG. 5 displays a side view of the apparatus 400 showing a preferred curvature of the handle 404 which allows each end of the device 400 to be used independently.

The present invention may also be combined with numerous prior-art devices designed to visually accentuate blood vessels for venipuncture. For example, LEDs have been pressed against the skin and light has been directed subcutaneously as in the device VENOSCOPE II. Under the appropriate ambient lighting conditions, a vein within that patch of skin will appear as a dark line. Accordingly, the present invention may include LEDs or other light sources that assist in the identification of a vein to be punctured.

The present invention is particularly useful for novices in venipuncture technique. It is also valuable for the experienced practitioner in that it would help locate and accentuate veins that are difficult to visualize. Finally, as detailed above, the present invention is further beneficial in stabilizing veins that are subject to "rolling" or "jumping" away from the needle during the venipuncture.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. An apparatus for aiding with venipuncture, comprising:
   a body, wherein said body includes a handle and wherein said body has a bottom and a top; and
   a plurality of tines disposed at an end of said body, wherein said plurality of tines are disposed roughly parallel to one another and are disposed roughly parallel to said handle from said end to a point where said plurality of tines turn towards the top of said body at which point said plurality of tines form a portion of said body, further wherein said plurality of tines includes a non-uniform distance between individual tines.

2. The apparatus of claim 1, wherein said portion of said body formed by said plurality of tines defines a scalloped out portion on the bottom of said apparatus.

3. The apparatus of claim 1, including three tines.

4. The apparatus of claim 1, including four tines.

5. The apparatus of claim 1, wherein said handle is curved.

6. The apparatus of claim 1, further comprising a light source, wherein said light source is adapted to accentuate an appearance of a vein to be punctured.

7. The apparatus of claim 1, wherein said tines are between about 2.5 centimeters and about 5 centimeters in length.

8. The apparatus of claim 7, wherein said tines are about 4 centimeters in length.

9. The apparatus of claim 1, wherein the distance between said tines varies between about 6 millimeters and about 9 millimeters.

10. A method of performing venipuncture, comprising the steps of:
    pressing an apparatus against the skin of a patient, wherein said apparatus comprises:
      a body, wherein said body includes a handle and wherein said body has a bottom and a top;
      a plurality of tines, wherein said plurality of tines are disposed roughly parallel to one another and are disposed roughly parallel to said handle, further wherein said plurality of tines are disposed at a first end of said body; and
      a portion of said body where said plurality of tines join said body, wherein said portion of said body on said bottom of said apparatus between plurality of tines is scalloped out;
    wherein said pressing step comprises pressing at least two tines against the skin of a patient, wherein said at least two tines sit astride a vein, wherein said pressing is achieved using said handle; and
    piercing a vein with a hypodermic needle.

11. The method of claim 10, wherein said handle is curved.

12. The method of claim 10, including three tines.

13. The method of claim 10, including four tines.

14. The method of claim 10, wherein said apparatus further comprises a light source, wherein said light source is adapted to accentuate the appearance of said vein.

* * * * *